US012551726B1

United States Patent
Zhang et al.

(12) United States Patent

(10) Patent No.: US 12,551,726 B1

(45) Date of Patent: Feb. 17, 2026

(54) REAL-TIME HUMAN POSTURE TRACKING AND CALIBRATION SYSTEM FOR TUMOR RADIOTHERAPY

(71) Applicant: Guangzhou Institute of Cancer Research, the Affiliated Cancer Hospital, Guangzhou Medical University, Guangzhou (CN)

(72) Inventors: Guoqian Zhang, Guangzhou (CN); Xin He, Guangzhou (CN); Shuxu Zhang, Guangzhou (CN); Linjing Wang, Guangzhou (CN); Shuyu Wu, Guangzhou (CN); Yuliang Liao, Guangzhou (CN); Lu Zhou, Guangzhou (CN); Huijun Li, Guangzhou (CN); Lu Yang, Guangzhou (CN); Ruihao Wang, Guangzhou (CN); Liangqian Gou, Guangzhou (CN)

(73) Assignee: Guangzhou Institute of Cancer Research, the Affiliated Cancer Hospital, Guangzhou Medical University, Guangzhou (CN)

( * ) Notice: Subject to any disclaimer, the term of this patent is extended or adjusted under 35 U.S.C. 154(b) by 0 days.

(21) Appl. No.: 19/096,945

(22) Filed: Apr. 1, 2025

Related U.S. Application Data

(63) Continuation of application No. PCT/CN2024/117775, filed on Sep. 9, 2024.

(30) Foreign Application Priority Data

Aug. 19, 2024 (CN) ........................ 202411133229.2

(51) Int. Cl.
*A61N 5/10* (2006.01)

(52) U.S. Cl.
CPC ........... *A61N 5/107* (2013.01); *A61N 5/1049* (2013.01); *A61N 5/1075* (2013.01)

(58) Field of Classification Search
CPC .............. A61G 13/1275; A61G 13/127; A61G 13/1265; A61G 13/126; A61G 13/02;
(Continued)

(56) References Cited

U.S. PATENT DOCUMENTS 10,737,118 B2 * 8/2020 Mostafavi .............. A61B 6/037
2001/0049475 A1 * 12/2001 Bucholz ................. A61B 5/055 378/65

(Continued)

FOREIGN PATENT DOCUMENTS

CN 109276820 A 1/2019
CN 111785349 A 10/2020

(Continued)

OTHER PUBLICATIONS

Retrieval report-First search dated Jan. 24, 2025 in SIPO application No. 202411133229.2.

(Continued)

*Primary Examiner* — Christopher Koharski
*Assistant Examiner* — Helene Bor
(74) *Attorney, Agent, or Firm* — Pilloff Passino & Cosenza LLP; Rachel Pilloff; Sean Passino

(57) ABSTRACT

A real-time human posture tracking and calibration device and a system for tumor radiotherapy are provided, which may replace the traditional treatment bed of a linear accelerator. For tumor targets in areas such as the head and neck that do not move with respiration, the system tracks changes in the skin external contour and the static position of the tumor. For tumors in the chest and abdomen that are significantly affected by respiration, the system first tracks changes in the skin external contour and then compensates
(Continued)

for the displacement of the tumor target moving with respiration.

4 Claims, 5 Drawing Sheets

(58) Field of Classification Search
CPC ...... A61G 13/08; A61G 13/12; A61N 5/1049; A61N 5/1075; A61N 5/107
See application file for complete search history.

(56) References Cited

U.S. PATENT DOCUMENTS

| | | | | |
|---|---|---|---|---|
| 2005/0028280 | A1 * | 2/2005 | Nakamura | A61B 6/04 5/601 |
| 2005/0138732 | A1 * | 6/2005 | Erbel | A61N 5/1049 5/601 |
| 2006/0072699 | A1 * | 4/2006 | Mackie | A61B 6/032 378/4 |
| 2013/0303898 | A1 * | 11/2013 | Kinahan | A61B 6/032 600/407 |
| 2019/0015685 | A1 * | 1/2019 | Ostyn | A61G 13/02 |
| 2023/0036916 | A1 | 2/2023 | Stringer, III et al. | |
| 2024/0207646 | A1 * | 6/2024 | Stahl | A61N 5/1045 |

FOREIGN PATENT DOCUMENTS

| | | | | | |
|---|---|---|---|---|---|
| CN | 116139419 | A | | 5/2023 | |
| GB | 997836 | A | * | 7/1965 | F16C 7/02 |

OTHER PUBLICATIONS

Notification to Grant Patent Right for Invention dated Jan. 28, 2025 in SIPO application No. 202411133229.2.
Ju Yongjian et al., "The comparison of the targets and the reconstructed three dimensional contours at different respiratory phases of celiac tumor patient," Journal of Nantong University (Medical Sciences), Sep. 15, 2007, pp. 365-367, vol. 27, No. 5. (DOI: 10.3969/j.issn.1674-7887.2007.05.016) Full text Claims involved: 1-5.

* cited by examiner

REAL-TIME HUMAN POSTURE TRACKING AND CALIBRATION SYSTEM FOR TUMOR RADIOTHERAPY

CROSS-REFERENCE TO RELATED APPLICATIONS

This application is a continuation of PCT/CN2024/117775, filed on Sep. 9, 2024 and claims priority to Chinese Patent Application No. 202411133229.2, filed on Aug. 19, 2024 the contents of which are hereby incorporated by reference.

TECHNICAL FIELD

The application belongs to the technical field of tumor radiotherapy, and particularly relates to a real-time human posture tracking and calibration system for tumor radiotherapy.

BACKGROUND

Radiotherapy is a therapy that uses high-energy rays to irradiate malignant tumors to inhibit their growth and cause death, referred to as radiotherapy. The basic principle of radiotherapy is to destroy malignant tumors while preserving normal tissue.

At present, before performing radiotherapy on patients, it is necessary to use posture fixation devices such as thermoplastic film, foam rubber, or vacuum bags to fix the tumor area of the patient's body to prevent movement during irradiation, thereby ensuring accurate irradiation of the target area. However, the following problems exist in the application of these fixation devices:

First, as radiotherapy and concurrent treatments such as chemotherapy progress, patients often experience weight loss and irregular reduction in the volume of the external body contour. At this time, traditional posture fixation devices such as thermoplastic film, foam rubber, or vacuum bags often have gaps with the body surface, making it difficult to achieve good adhesion or wrapping. At this time, positioning through the crosshairs on the fixation device surface results in poor fixation of the human body or tumor target area. The disclosure, on one hand, adjusts the support components in the fixation device by tracking changes in the skin external contour to achieve posture calibration during radiotherapy.

In addition, due to factors such as respiratory motion, patients with thoracic and abdominal tumors inevitably experience some posture or tumor changes between different radiotherapy sessions and during a single radiotherapy session, leading to changes in the position of the tumor target area and affecting the accuracy of the irradiation position during radiotherapy.

Clinically, the irradiation field is often expanded to ensure that the tumor's movement range remains within the field, thereby preventing the tumor from missing the target. However, this approach increases the dose to normal tissues, raising the probability of normal tissue complications and potentially affecting the patient's quality of life. On the other hand, to monitor the spatial position of the body surface or internal tumor target area in real time, systems such as 4-Dimensional Cone Beam Computed Tomography (4DCBCT), 4-Dimensional Magnetic Resonance Imaging (4DMR), real-time ultrasound, optical surface guidance, or electromagnetic guidance are currently used in clinical practice. When these systems detect that the tumor position is "off-target," i.e., outside the irradiation field, the radiation beam stops, and when the tumor target area returns to the irradiation field, the radiation beam resumes, i.e., gated radiotherapy. However, this method has low radiation utilization efficiency, longer treatment times, poor patient compliance, and affects treatment efficacy. Additionally, the treatment bed equipped with a linear accelerator may also be used to correct positioning errors. The current treatment bed for positioning error calibration may adjust up to six dimensions. Before radiotherapy, imaging guidance technology may detect the position deviation of the tumor target area, and the treatment bed may perform online corrections. The six-dimensional treatment bed has linear movements in x, y, and z directions and rotational movements around the x, y, and z directions, allowing adjustment of the patient's posture in six degrees of freedom to correct the aforementioned position errors. However, this adjustment is based on the premise that the posture fixation device may stably fix the patient's posture. If the external body contour undergoes irregular changes of varying degrees, the application of the six-dimensional bed may not achieve precise adjustment of the patient's posture, making it difficult to achieve accurate irradiation of the tumor target area.

SUMMARY

The technical problem to be solved by the disclosure is to provide a real-time human posture tracking and calibration system for tumor radiotherapy, which may achieve precise irradiation of the tumor target area by tracking real-time position changes of the tumor target area and adjusting the support components in real time to correct the human body's centroid position, thereby compensating for the real-time displacement of the tumor target area and achieving precise irradiation of the tumor.

To achieve the above purpose, the disclosure adopts the following technical solution:

a real-time human posture tracking and calibration system for tumor radiotherapy, including: a posture reconstruction device, a posture control device, a posture tracking device, and a U-shaped base; where a telescopic support rod is arranged in a matrix on the U-shaped base to form a support matrix, a bottom of each of the telescopic support rods is equipped with a stepper motor for precisely controlling an extension length of each of the telescopic support rods through a lead screw; an upper end of each of the telescopic support rods is connected to a non-metallic circular support ball, the support ball is wrapped with a silicone layer and contains a non-metallic material, capable of being detected by a millimeter-wave detector at a foot of a treatment bed; the foot of the treatment bed is equipped with a millimeter-wave detector, the millimeter-wave detector is capable of scanning all the support balls by emitting millimeter waves to detect a spatial position of each of the support balls; the U-shaped base is equipped with support gears underneath, and a rotation of the gears drives the U-shaped base to rotate on a cross-section of the base.

Optionally, the real-time human posture tracking and calibration system for tumor radiotherapy is used for positioning in location of head and neck, chest, abdomen, or limbs all over the body.

Optionally, the posture reconstruction device is used to obtain 4DCT images or Computed Tomography (CT) positioning images collected during simulation CT scanning, and calculates a height information of the support balls corresponding to the positions of the support rods in the support matrix based on the spatial coordinates of each pixel in the 4DCT or the CT positioning images.

Optionally, after the height information of all support balls in the support matrix is transmitted to a posture control device, the control device controls each motor in the support matrix to drive the corresponding support rod to extend or retract to the required length, pushing the support balls at the ends of the support rods to rise to the predetermined height.

Optionally, during online surface tracking, the posture tracking device detects the support balls via the millimeter-wave detector, i.e., detects the spatial position information of the support balls connected to all support rods in the support matrix, and reconstructs a partial virtual human external contour and obtains the geometric centroid position of the virtual human external contour using the spatial position information of the support balls in contact with the human body; the posture tracking device then compares this information with the spatial position information of the support balls calculated by the posture reconstruction device, calculates the spatial position deviation of each ball in the matrix, and transmits the deviation data to the posture control device;

the posture control device controls the U-shaped base to rotate or move in the forward or backward direction via gear drive to correct the rotational deviation and the head-to-foot direction error, and then adjusts the extension length of the support rods based on the spatial position deviation of the support balls to adjust the position of the support balls.

Optionally, the posture reconstruction device segments the skin external contour based on real-time online image guidance device data obtained from the patient's real-time online imaging information; the posture reconstruction device performs rigid registration between the segmented CT image skin external contour and the simulation positioning image skin external contour to obtain the patient's positioning rotational deviation and head-to-foot direction error data; the posture reconstruction device also reads the spatial coordinates of each pixel in the CT image skin external contour, and then calculates the spatial position information of all support balls that may contact the human body based on the spatial position of each voxel in the real-time external contour, thereby obtaining the spatial position deviation of each support ball compared to the initial posture reconstruction.

Optionally, the real-time online image guidance device monitors the real-time spatial position information of each voxel in the patient's tumor target area, and the posture reconstruction device segments the tumor target area contour and obtains the geometric centroid displacement vector field of the real-time tumor contour;

the posture tracking device compensates for the displacement of the tumor target area;

the posture tracking device calculates the real-time motion vector field of each support ball in the support matrix based on the geometric centroid displacement vector field of the virtual human external contour; the real-time vertical displacement of all support balls is adjusted based on the geometric centroid displacement compensation of the real-time tumor contour, ultimately achieving real-time tracking and calibration of human posture.

Optionally, the displacement compensation for the tumor target area by the posture tracking device is specifically: calculating the geometric centroid of the virtual human external contour, which is reconstructed by the posture tracking device via the millimeter-wave detector detecting the position of the support balls; based on the geometric centroid displacement vector field of the tumor contour, calculating the motion compensation displacement vector field of the centroid relative to its static position, and then calculating the geometric centroid displacement vector field of the virtual external contour to perform the displacement compensation for the position changes of the tumor target area.

The disclosure may achieve real-time adjustment of the patient's posture during radiotherapy without expanding the irradiation field. By compensating for the real-time displacement of the human skin external contour and the tumor target area, the tumor target area is always kept within the irradiation field, reducing normal tissue side effects, improving the efficiency of linear accelerator treatment, and ensuring the patient's treatment efficacy. When using this system and device for radiotherapy, the production of traditional posture fixation devices is no longer necessary. During simulation CT scanning, complex posture fixation devices are also no longer required, and tumor patients may meet the positioning requirements for radiotherapy. This device and system may replace the traditional treatment bed of a linear accelerator (which only has four or six degrees of freedom) and achieve real-time tracking and calibration of human posture or tumor targets with more than six degrees of freedom through a matrix of independently adjustable support components.

BRIEF DESCRIPTION OF THE DRAWINGS

To more clearly illustrate the embodiments of the disclosure or the prior art, the following will briefly introduce the drawings required for describing the embodiments or the prior art. Obviously, the drawings in the following description are only some embodiments of the disclosure. For those skilled in the art, other drawings may be obtained based on these drawings without creative effort.

DETAILED DESCRIPTION OF THE EMBODIMENTS

The following will clearly and completely describe the technical solutions in the embodiments of the disclosure with reference to the accompanying drawings. Obviously, the described embodiments are only a part of the embodiments of the disclosure, not all of them. Based on the embodiments of the disclosure, all other embodiments obtained by those skilled in the art without creative effort shall fall within the protection scope of the disclosure.

To make the above purposes, features, and advantages of the disclosure more apparent and understandable, the following will further describe the disclosure in detail with reference to the accompanying drawings and specific embodiments.

Embodiment 1

Figure 1:
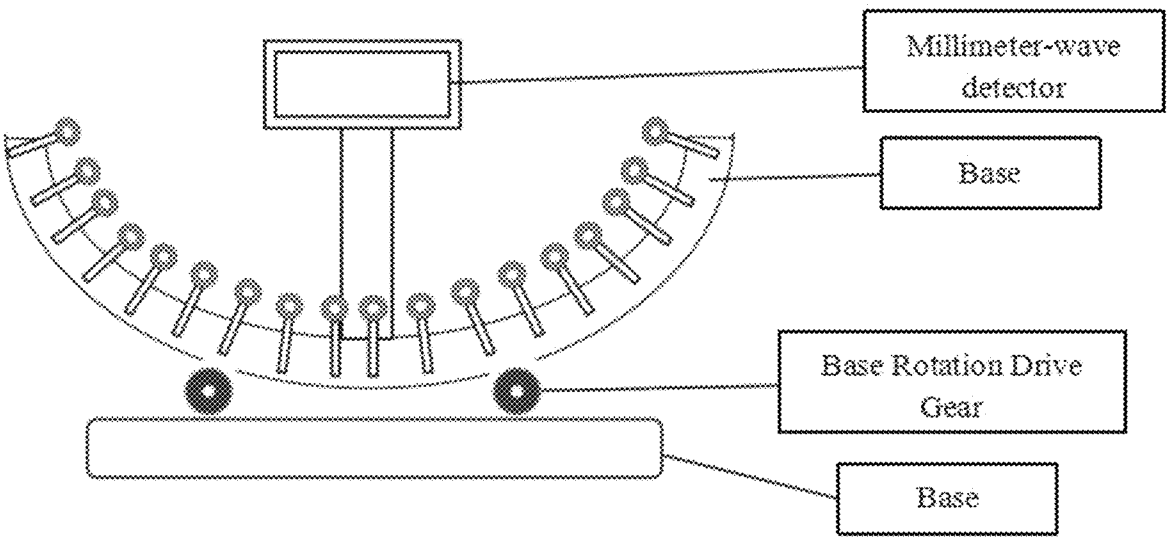
FIG. 1 is a schematic diagram of the posture tracking and adjustment device of the real-time human posture tracking and calibration system for tumor radiotherapy.
Figure 2:
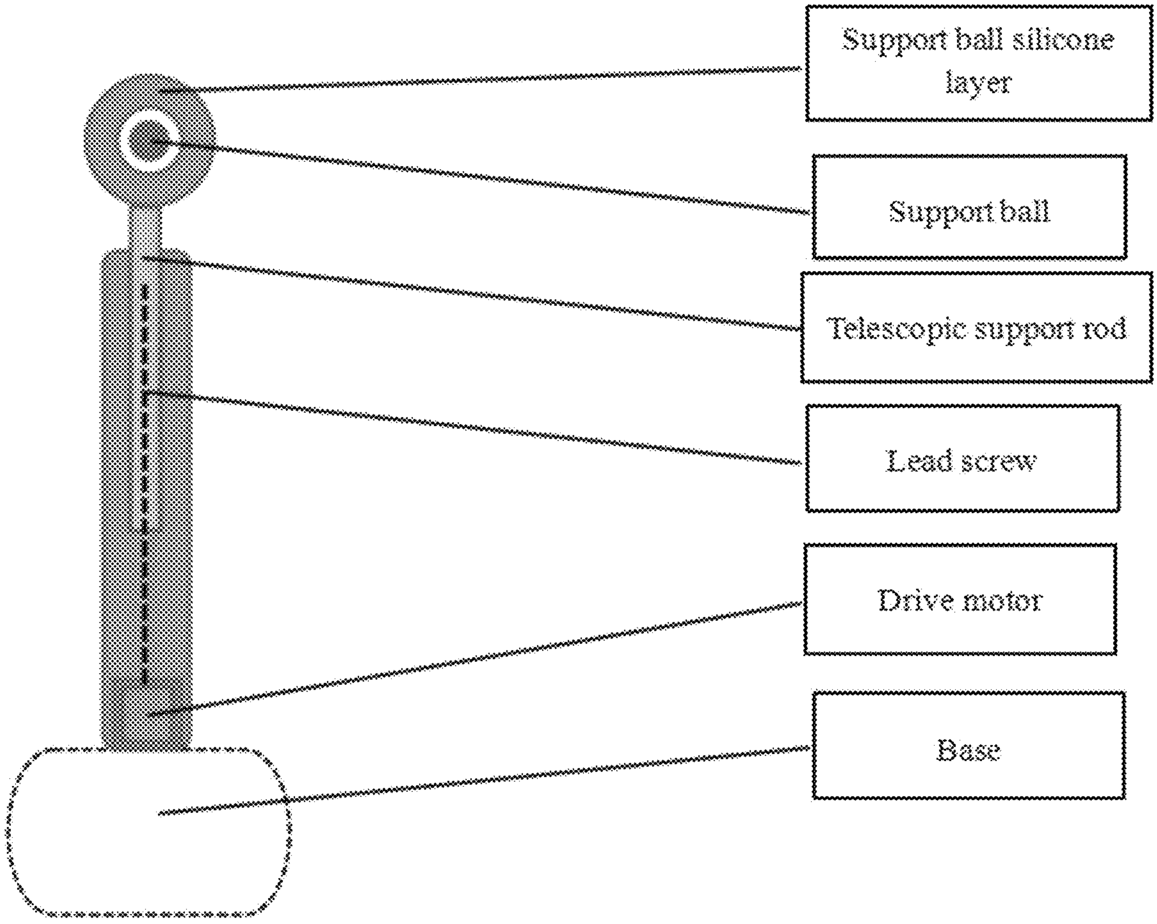
FIG. 2 is a schematic diagram of the support components of the real-time human posture tracking and calibration system for tumor radiotherapy.
Figure 3:
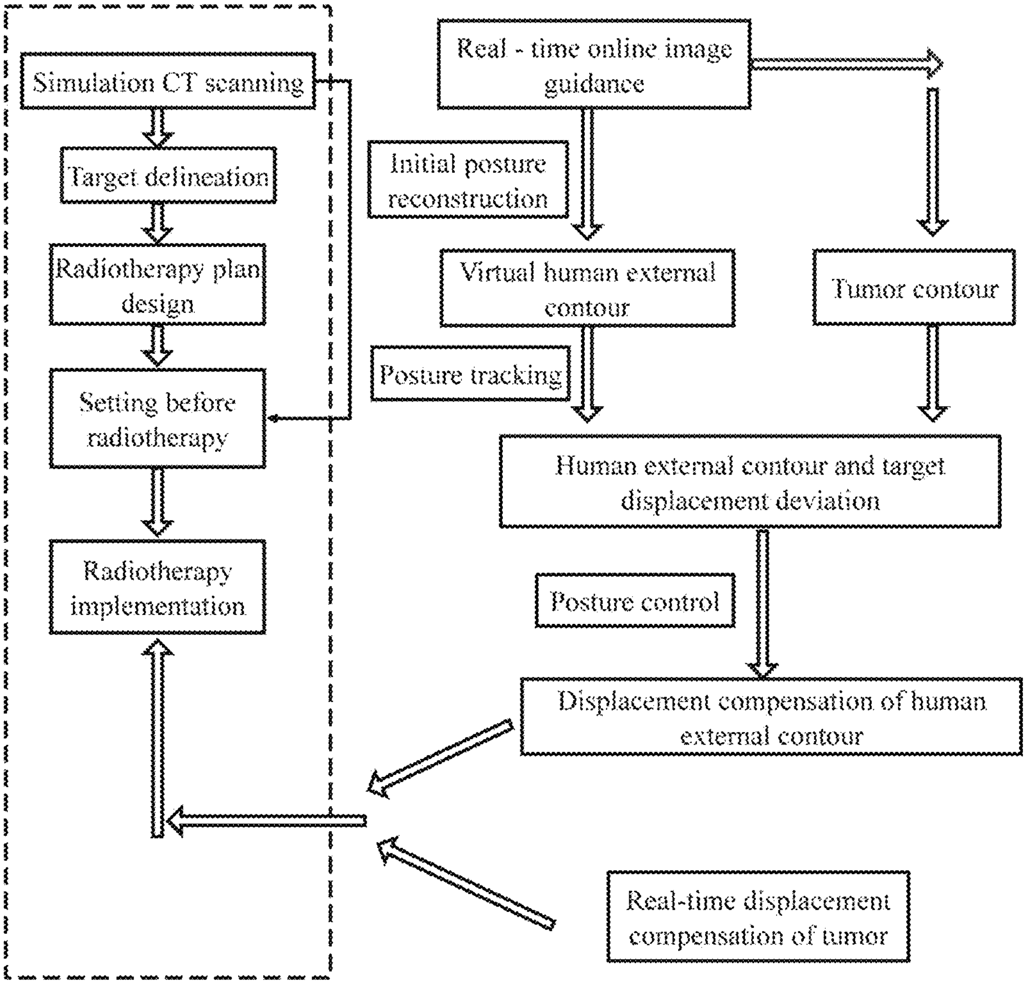
FIG. 3 is a workflow diagram of the real-time human posture tracking and calibration system for tumor radiotherapy according to an embodiment of the disclosure.
Figure 4:
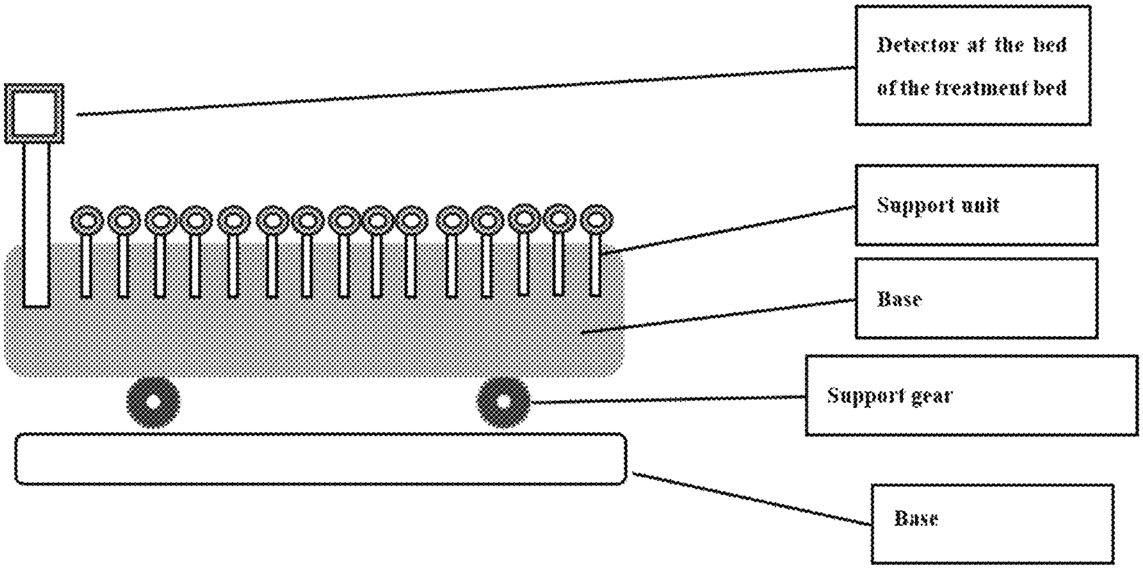
FIG. 4 is a schematic diagram of the treatment bed of the real-time human posture tracking and calibration system for tumor radiotherapy.
Figure 5:
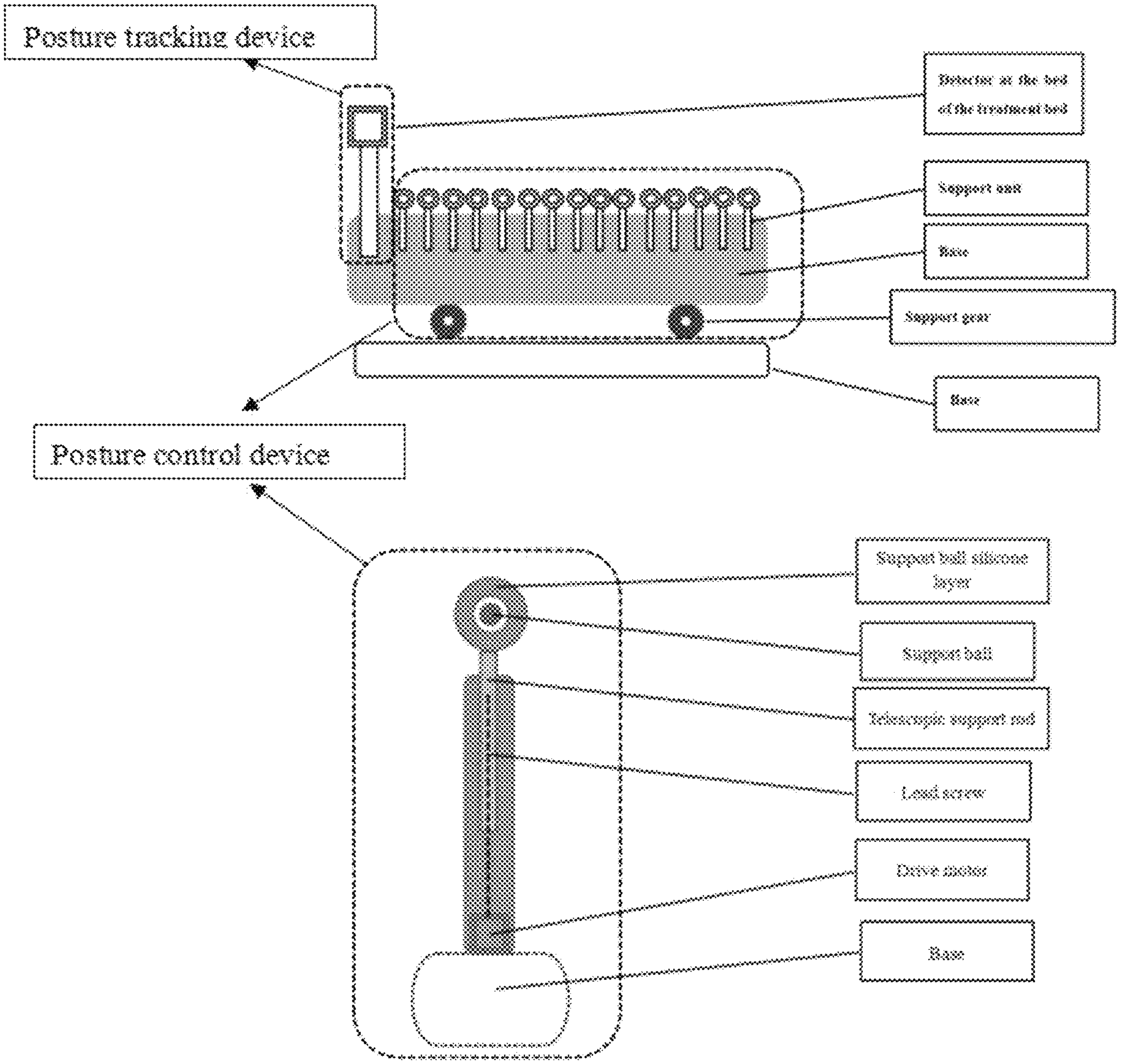
FIG. 5 is a schematic diagram of the posture control device and posture tracking device of the real-time human posture tracking and calibration system for tumor radiotherapy according to an embodiment of the disclosure.

The embodiment of the disclosure provides a real-time human posture tracking and calibration system for tumor radiotherapy, including: a posture reconstruction device, a posture control device, a posture tracking device, and a U-shaped base. As shown in FIG. 1 and FIG. 2, telescopic support rods are arranged in a matrix on the U-shaped base to form a support matrix, the bottom of each telescopic support rod is equipped with a stepping drive motor, which precisely controls the extension and retraction of the support rod via a lead screw; the upper end of each telescopic support rod is connected to a non-metallic circular support ball, which is wrapped in a silicone layer and contains a non-metallic material detectable by a millimeter-wave detector at the end of the treatment bed. The treatment bed is equipped with a millimeter-wave detector at its end, which scans all support balls by emitting millimeter waves to detect the spatial position of each ball; the U-shaped base is equipped with support gears at the bottom, which rotate to drive the U-shaped base to rotate in the transverse plane of the base. The real-time human posture tracking and calibration system for tumor radiotherapy may be used for positioning in the head and neck, chest, abdomen, or limbs; wherein, it is divided into Zone A (head and neck), Zone B (chest, abdomen, and pelvis), and Zone C (lower limbs), with higher support matrix density in Zones A and C.

The implementation of the real-time human posture tracking and calibration system for tumor radiotherapy is divided into three stages:

Stage 1: Posture Data Analysis

First, during simulation CT scanning, 4DCT images (for thoracic and abdominal tumors) or conventional CT positioning images (for head and neck tumors or pelvic tumors) are collected from tumor patients, and these image data are transmitted to the posture reconstruction device, which automatically or manually segments the skin external contour and the three-dimensional tumor volume contour; for 4DCT images, after segmenting the three-dimensional tumor volume contour, the geometric centroid displacement vector field of the tumor in multiple phases may be obtained.

Then, the human posture support matrix coordinates are reconstructed. To establish the CT spatial coordinate system, three lead points (Mark points) are typically attached to the body surface during CT positioning scans to be identified in the CT images. Based on these Mark points, the origin of the image spatial coordinates (x=0, y=0, z=0) may be determined. In the y-direction, the pixel coordinates of the body surface contour (mainly the lower surface of the human body) corresponding to the Mark point are (x=0, y=y', z=z'). In the device of the present disclosure, the support matrix will also set a matrix origin in the corresponding zone (A, B, C) based on the tumor location. The position and height information of the support ball at the end of the support rod at the matrix origin will match the spatial position information of the body surface contour pixel (mainly the lower surface of the human body) corresponding to the current patient's CT image spatial coordinate origin, i.e., the coordinates of the support ball at the end of the support rod at the matrix origin are (x=0, y=y', z=z'). At this point, the reconstruction of the support matrix coordinates is completed.

Then, the posture reconstruction device reads the spatial coordinate values of each pixel in the CT image skin external contour (mainly the lower surface of the human body) and calculates the height information of the support balls corresponding to the positions of the support rods in the support matrix. This information is simultaneously transmitted to the posture control device. At this point, the posture data analysis stage is completed.

Stage 2: Posture Support Matrix Reconstruction

After the height information of all support balls in the support matrix is transmitted to the posture control device, the control device controls each motor in the support matrix to drive the corresponding support rod to extend or retract to the required length, pushing the support balls at the ends of the support rods to rise to the predetermined height.

At this point, the reconstruction of the posture support matrix based on the patient's CT positioning scan images is completed.

Stage 3: Online Surface Tracking

According to the conventional radiotherapy workflow, after target delineation and treatment planning (for thoracic and abdominal tumors, if 4DCT scanning has been performed, the time-weighted median image may be used for treatment planning; for head and neck or pelvic tumors, conventional CT positioning images may be used for treatment planning), the patient enters the linear accelerator room and begins pre-treatment positioning. After the completion of the posture support matrix reconstruction in the second stage, the patient may lie down or recline on the support balls of the support matrix in the same position as during the CT simulation, thus achieving the same posture as during the simulation.

First, the posture tracking device detects the support balls via the millimeter-wave detector, i.e., detects the spatial position information of the support balls connected to all support rods in the support matrix. Using the spatial position information of the support balls in contact with the human body, a partial virtual human external contour may be reconstructed, and the geometric centroid position of the virtual human external contour may be obtained. This information is compared with the spatial position information of the support balls calculated by the posture reconstruction device, and the spatial position deviation of each ball in the matrix is calculated. This deviation data is then transmitted to the posture control device for adjustment until the two match. At this point, the reconstruction of the positioning posture based on the simulation CT images is completed.

Then, real-time online imaging devices such as conventional Cone Beam Computed Tomography (CBCT), 4DCBCT, 4DMR, or real-time ultrasound monitor and obtain the patient's real-time online imaging information. This imaging data is again transmitted to the posture reconstruction device, which automatically or manually segments the skin external contour, initiating the following two processes:

- on one hand, the posture reconstruction device performs rigid registration between the segmented CT image skin external contour and the simulation positioning image skin external contour to obtain the patient's positioning rotational deviation and head-to-foot direction error data.

On the other hand, the posture reconstruction device reads the spatial coordinate values of each pixel in the CT image skin external contour and calculates the spatial position information of all support balls that may contact the human body based on the spatial position of each voxel in the real-time external contour, thereby obtaining the spatial position deviation of each support ball compared to the initial posture reconstruction.

Then, the posture reconstruction device transmits the position deviation data obtained from the above two processes to the posture control device. The posture control device initiates the following control process:

the U-shaped base is controlled to rotate or move forward or backward via gear drive to correct the positioning rotational deviation and head-to-foot direction error data. Then, based on the spatial position deviation of the support balls, the support matrix adjusts the extension length of the support rods under motor drive, thereby adjusting the position of the support balls. At this point, the tracking and calibration of human posture based on the skin external contour are completed.

At the same time, real-time online imaging devices such as 4DCBCT, 4DMR, or real-time ultrasound monitor the real-time spatial position information of each voxel in the patient's tumor target area. The posture reconstruction device segments the tumor target area contour and obtains the geometric centroid displacement vector field of the real-time tumor contour.

Then, the posture tracking device compensates for the displacement of the tumor target area as follows: First, the geometric centroid of the virtual human external contour is calculated. This virtual human external contour is reconstructed by the posture tracking device via the millimeter-wave detector detecting the position of the support balls. Then, based on the geometric centroid displacement vector field of the tumor contour, the motion compensation displacement vector field of the centroid relative to its static position is calculated, and the geometric centroid displacement vector field of the virtual external contour is calculated to compensate for the position change of the tumor target area.

Subsequently, the posture tracking device calculates the real-time motion vector field of each support ball in the support matrix based on the geometric centroid displacement vector field of the virtual human external contour. The real-time vertical displacement of all support balls is adjusted based on the geometric centroid displacement compensation of the real-time tumor contour, ultimately achieving real-time tracking and calibration of human posture.

The real-time calibration in the embodiment of the present disclosure has two scenarios:

1. when the spatial position of tumors in the chest and abdomen, such as the lungs, liver, or breast, changes with respiratory motion; the embodiment of the present disclosure ensures that the target area remains within the irradiation field by real-time correction of the human body position. Currently, clinically, the irradiation field may only be expanded to ensure that the tumor target area does not miss the target when moving with respiration, thereby ensuring sufficient radiation dose to the tumor. However, expanding the irradiation field results in more normal tissues around the tumor, such as lung or liver tissues, being included in the irradiation field, which may lead to more normal tissue complications. The embodiment of the present disclosure may minimize the irradiation field by real-time adjustment of the human body position to offset or minimize the relative movement range of the tumor, reducing the radiation dose to normal tissues and thus lowering the probability of normal tissue complications. It should be noted that when the spatial position of the tumor changes with respiratory motion, the external body contour often does not undergo involuntary changes. The embodiment of the present disclosure links the internal tumor position change information with the positioning device, using the system's matrix-arranged supports and support balls to real-time adjust the human body position, thereby keeping the tumor's spatial position and the irradiation field relatively fixed.
2. For relatively rigid human tissues in the head and neck, tumors usually do not move with respiration during radiotherapy, and only the initial radiotherapy positioning accuracy needs to be ensured. In the implementation of this technology, only the skin external contour and static tumor position need to be tracked and adjusted. Compared to a flat base, the U-shaped base in the embodiment of the present disclosure can better match the curved contour of the human body's side, achieving a more enveloping positioning effect.

The above-described embodiments are only preferred embodiments of the present disclosure and do not limit the scope of the disclosure. Without departing from the design spirit of the present disclosure, various modifications and improvements made by those skilled in the art to the technical solutions of the present disclosure shall fall within the protection scope defined by the claims of the present disclosure.

What is claimed is:

1. A real-time human posture reconstruction, control, tracking and calibration system for tumor radiotherapy, comprising: a posture reconstruction module, a posture control device, a posture tracking device, a treatment bed, an image device, wherein the treatment bed comprising: a module, a millimeter-wave detector, a support ball, a telescopic support rod and a U-shaped base;

wherein telescopic support rods are arranged in a matrix on the U-shaped base to form a support matrix, a bottom of each of the telescopic support rods is equipped with a stepper motor for controlling an extension length of each of the telescopic support rods through a lead screw;

wherein an upper end of each of the telescopic support rods is connected to a non-metallic circular support ball, the support balls are wrapped with a silicone layer and contains a non-metallic material, wherein the millimeter-wave detectors are configured to scan all the support balls by emitting millimeter waves to detect a spatial position of each of the support balls;

wherein the U-shaped base is equipped with support gears underneath, and a rotation of the support gears drives the U-shaped base to rotate on a cross-section of the base;

in online surface tracking, the posture tracking device detects the support balls through the millimeter-wave detector, that detects height spatial position information corresponding to positions of all the support balls connected to the support rods in the support matrix, and reconstructs a partial virtual human external contour using spatial position information of the support balls in contact with a human body, and obtain a geometric centroid position of a virtual human external contour;

wherein the posture reconstruction module calculates the height spatial position information of all the support balls connected to the support rods in the support matrix for position verification, calculates a spatial position deviation of each of the support balls in the matrix, and then transmits the spatial position deviation to the posture control device;

wherein the posture control device is configured to control the U-shaped base to rotate angularly or move in a forward and backward direction through support gears, correcting a rotational deviation of positioning and an error in a head-to-foot direction, and then the support matrix changes the extension length of the support rods to adjusts positions of the support balls, based on the spatial position deviation of the support balls under the stepper motor;

wherein the posture reconstruction module segments a skin external contour based on real-time online image guidance of a patient obtained by the real-time online image guidance device;

wherein the posture reconstruction module rigidly registers segmented CT image skin external contour with a simulated positioning image's skin external contour to obtain the positioning rotational deviation and head-to-foot direction error data of the patient;

wherein the posture reconstruction module simultaneously reads the real-time spatial coordinate information of each pixel point of the CT image skin external contour, then calculates real-time spatial coordinate information of all support balls capable of contacting the human body using the spatial position of each voxel point of received real-time body surface external contour, and thereby obtains the spatial position deviation of each of the support balls from initial posture reconstruction;

wherein the real-time spatial coordinate information of each voxel point of a real-time tumor target area of the patient is monitored by the real-time online image guidance device, and the posture reconstruction module segments a tumor target area contour and obtains a geometric centroid displacement vector field of a real-time tumor contour;

wherein a displacement compensation for a tumor target area position is performed by the posture tracking device;

wherein the posture tracking device calculates a real-time motion vector field of each of the support balls in the support matrix based on the geometric centroid displacement vector field of the virtual human external contour; and wherein the step motors drive the support balls to perform the real-time lifting displacement according to the calculated motion vector field, thereby achieving real-time tracking and calibration of a human posture through compensation of the geometric centroid displacement of the real-time tumor contour.

2. The real-time human posture reconstruction, control, tracking and calibration system for tumor radiotherapy according to claim 1, wherein the posture reconstruction module is configured to obtain 4DCT images or CT positioning images collected during positioning CT scanning, and calculate height information of the support balls corresponding to the positions of the support rods in the support matrix based on the real-time spatial coordinate information of each pixel point in the 4DCT images or the CT positioning images.

3. The real-time human posture reconstruction, control, tracking and calibration system for tumor radiotherapy according to claim 2, wherein after the height information of all the support balls of the support rods in the support matrix is transmitted to the posture control device, the posture control device controls each motor in the support matrix, and each motor drives the support rods to extend or retract to a corresponding length, pushes the support balls at ends of the support rods to rise, making all the support balls reach a predetermined height.

4. The real-time human posture reconstruction, control, tracking and calibration system for tumor radiotherapy according to claim 3, wherein the displacement compensation for the tumor target area position by the posture tracking device is specifically: calculating geometric centroid of the virtual human external contour, wherein the virtual human external contour is obtained by detecting and reconstructing the positions of the support balls by the posture tracking device through the millimeter-wave detector; based on the geometric centroid displacement vector field of the tumor contour, calculating the motion compensation displacement vector field of the centroid relative to a stationary state, and then calculating the geometric centroid displacement vector field of the virtual external contour to perform the displacement compensation for position changes of the tumor target area.

* * * * *